United States Patent
Yamauchi et al.

(10) Patent No.: US 11,733,324 B2
(45) Date of Patent: Aug. 22, 2023

(54) MAGNETIC PARTICLE IMAGING SYSTEM AND MAGNETIC PARTICLE IMAGING METHOD

(71) Applicants: Mitsubishi Electric Corporation, Tokyo (JP); MITSUBISHI ELECTRIC RESEARCH LABORATORIES, INC., Cambridge, MA (US)

(72) Inventors: Kazuki Yamauchi, Tokyo (JP); Chungwei Lin, Cambridge, MA (US)

(73) Assignees: MITSUBISHI ELECTRIC CORPORATION, Tokyo (JP); MITSUBISHI ELECTRIC RESEARCH LABORATORIES, INC., Cambridge, MA (US)

( * ) Notice: Subject to any disclaimer, the term of this patent is extended or adjusted under 35 U.S.C. 154(b) by 0 days.

(21) Appl. No.: 17/483,809

(22) Filed: Sep. 24, 2021

(65) Prior Publication Data

US 2023/0099731 A1  Mar. 30, 2023

(51) Int. Cl.
*G01R 33/10* (2006.01)
*G01R 33/12* (2006.01)

(52) U.S. Cl.
CPC ......... *G01R 33/1276* (2013.01); *G01R 33/10* (2013.01)

(58) Field of Classification Search
CPC ............... G01R 33/00; G01R 33/0035; G01R 33/0023; G01R 33/0017; G01R 31/3191;
(Continued)

(56) References Cited

U.S. PATENT DOCUMENTS

2012/0126808 A1* 5/2012 Knopp ................. A61B 5/0515
324/301
2018/0017639 A1* 1/2018 Goodwill ........... G01R 33/1276
(Continued)

FOREIGN PATENT DOCUMENTS

EP  3 378 389 A1  9/2018
JP  5767225 B2  8/2015
(Continued)

OTHER PUBLICATIONS

Murase et al., "Development of a System for Magnetic Particle Imaging Using Neodymium Magnets and Gradiometer", Japanese Journal of Applied Physics, vol. 53, 2014, pp. 067001-1-067001-7.
(Continued)

*Primary Examiner* — Jermele M Hollington
*Assistant Examiner* — Taqi R Nasir
(74) *Attorney, Agent, or Firm* — Xsensus LLP (57) ABSTRACT

A magnetic particle imaging system includes a field free region generator and an excited magnetic field generator. The field free region generator generates a field free line with a direction of linear extension of a field free region as a direction of extension. The excited magnetic field generator generates an excited magnetic field in the field free line generated by the field free region generator. The excited magnetic field generator includes a first excited magnetic field generation unit and a second excited magnetic field generation unit. The first excited magnetic field generation unit and the second excited magnetic field generation unit are spaced from each other in the direction of extension of the field free line.

10 Claims, 9 Drawing Sheets

(58) Field of Classification Search
CPC .... G01R 33/1276; G01R 33/10; G01B 7/004; G01C 17/38; G06F 3/017; G06F 3/0346; G06F 3/012
See application file for complete search history.

(56) References Cited

U.S. PATENT DOCUMENTS

2018/0017641 A1\* 1/2018 Goodwill ............. A61B 5/0515
2019/0079149 A1 3/2019 Conolly et al.

FOREIGN PATENT DOCUMENTS

| JP | 2019-523115 A | 8/2019 |
| WO | 2011/021165 A1 | 2/2011 |
| WO | 2014/071196 A1 | 5/2014 |
| WO | 2018/013731 A1 | 1/2018 |

OTHER PUBLICATIONS

International Search Report and Written Opinion dated Oct. 26, 2022 in International Patent Application No. PCT/JP2022/026776, 13 pages.

\* cited by examiner

MAGNETIC PARTICLE IMAGING SYSTEM AND MAGNETIC PARTICLE IMAGING METHOD

BACKGROUND OF THE INVENTION

Field of the Invention

The present disclosure relates to a magnetic particle imaging system and a magnetic particle imaging method.

Description of the Background Art

Magnetic particle imaging (MPI) is under development as new non-destructive tomographic image diagnostic technology. Magnetic particle imaging detects, as a particle signal, a change in the magnetic field caused by excitation of magnetic particles in a subject as an excited magnetic field is applied from outside of the subject with the magnetic particles injected into the subject. Normally, a detection signal is mostly occupied by an excitation signal at a fundamental wave, and accordingly, a high-order harmonic is used as the particle signal.

To specify the location of magnetic particles in the subject, a magnetic field generation mechanism that generates a magnetic field different from the excited magnetic field generates a selective magnetic field that produces a region with a low magnetic field intensity and a region with a high magnetic field intensity. In particular, a region of the low field region which has a zero magnetic field is referred to as a field free region. Examples of the field free region include a field free point (FFP) and a field free line (FFL). In order to realize high-sensitivity measurements, the field free line (FFL) is used that is expected to have a signal strength an order of magnitude greater than that of the field free point (FFP).

Japanese Patent No. 5767225 (PTL 1) discloses a magnetic particle imaging system that generates a field free line (FFL). According to PTL 1, an excited magnetic field is applied perpendicular to the direction of extension of the field free line (FFL) so as to reduce a measurement time by the excited magnetic field serving not only to excite magnetic particles but also to scan the field free line (FFL). Being perpendicular herein refers to a case where an excited magnetic field is applied exactly perpendicularly, as well as a case where an excited magnetic field is applied to a component in the same direction as that of the selective magnetic field.

In the magnetic particle imaging system disclosed in PTL 1, the field free line (FFL) oscillates due to the excited magnetic field, and accordingly, the system function in the direction of excitation distributes across positive and negative values. This system function is a signal distribution function obtained by integrating a magnetization curve of particles, an excited magnetic field, a selective magnetic field, and sensitivity of a magnetic sensor. In this case, only a high-order harmonic component of one order is insufficient for reconstructing a particle distribution in the direction of the body axis of the subject from a measured signal.

SUMMARY OF THE INVENTION

The present disclosure has been made in view of the above problem, and an object thereof is to provide a magnetic particle imaging system and a magnetic particle imaging method that can reconstruct a particle distribution from a high-order harmonic component of at least one order.

A magnetic particle imaging system of the present disclosure is a magnetic particle imaging system that images magnetic particles in a field free region using an excited magnetic field for the magnetic particles. The magnetic particle imaging system includes a field free region generator and an excited magnetic field generator. The field free region generator generates a field free line with a direction of linear extension of the field free region as a direction of extension. The excited magnetic field generator generates an excited magnetic field in the field free line generated by the field free region generator. The excited magnetic field generator includes a first excited magnetic field generation unit and a second excited magnetic field generation unit. The first excited magnetic field generation unit and the second excited magnetic field generation unit are spaced from each other in the direction of extension of the field free line.

In the magnetic particle imaging system according to the present disclosure, the first excited magnetic field generation unit and the second excited magnetic field generation unit are spaced from each other in the direction of extension of the field free line. This enables reconstruction of a particle distribution from a high-order harmonic component of at least one order.

The foregoing and other objects, features, aspects and advantages of the present disclosure will become more apparent from the following detailed description of the present disclosure when taken in conjunction with the accompanying drawings.

DESCRIPTION OF THE PREFERRED EMBODIMENTS

The embodiment will now be described with reference to the drawings. The same or corresponding parts in the drawings have the same reference characters allotted, and description thereof will not be repeated.

A magnetic particle imaging system 10 according to an embodiment will be described with reference to FIG. 1. Magnetic particle imaging system 10 according to the embodiment is a magnetic particle imaging system that images magnetic particles in a field free region using an excited magnetic field for the magnetic particles.

Figure 1:
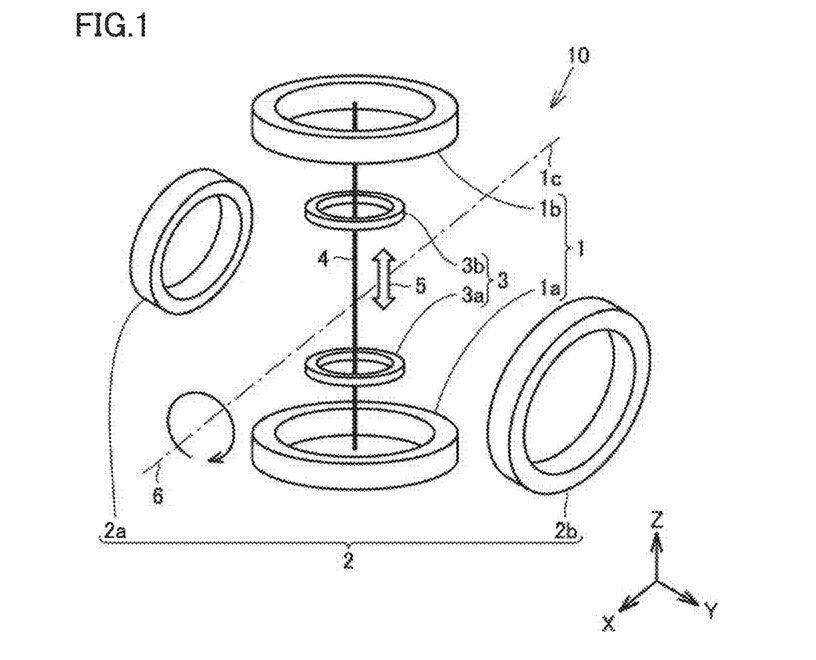
FIG. 1 is a perspective view schematically showing a configuration of a magnetic particle imaging system according to an embodiment.

As shown in FIG. 1, magnetic particle imaging system 10 according to the embodiment includes an excited magnetic field generator 1, a field free region generator 2, and a magnetic sensor 3.

Excited magnetic field generator 1 includes a first excited magnetic field generation unit 1*a* and a second excited magnetic field generation unit 1*b*. Field free region generator 2 includes a first field free region generation unit 2*a* and a second field free region generation unit 2*b*. Magnetic sensor 3 includes a first magnetic sensor unit 3*a* and a second magnetic sensor unit 3*b*.

Field free region generator 2 is configured to generate a gradient magnetic field in the direction in which first field free region generation unit 2*a* and second field free region generation unit 2*b* are opposed to each other. The gradient magnetic field forms, in an examination region, a high field region in which a magnetic particle cannot respond to excited magnetic field 5 due to magnetic saturation, and a low field region in which a magnetic particle can respond to excited magnetic field 5. The low field region in which a magnetic particle can respond to excited magnetic field 5 is referred to as a field free region. Note that the zero magnetic field is exactly obtained only at the center of the low field region. A permanent magnet, a permanent magnet with a yoke, an electromagnet including only a coil, an electromagnet including a coil with a yoke, or the like is used for field free region generator 2.

Figure 2:
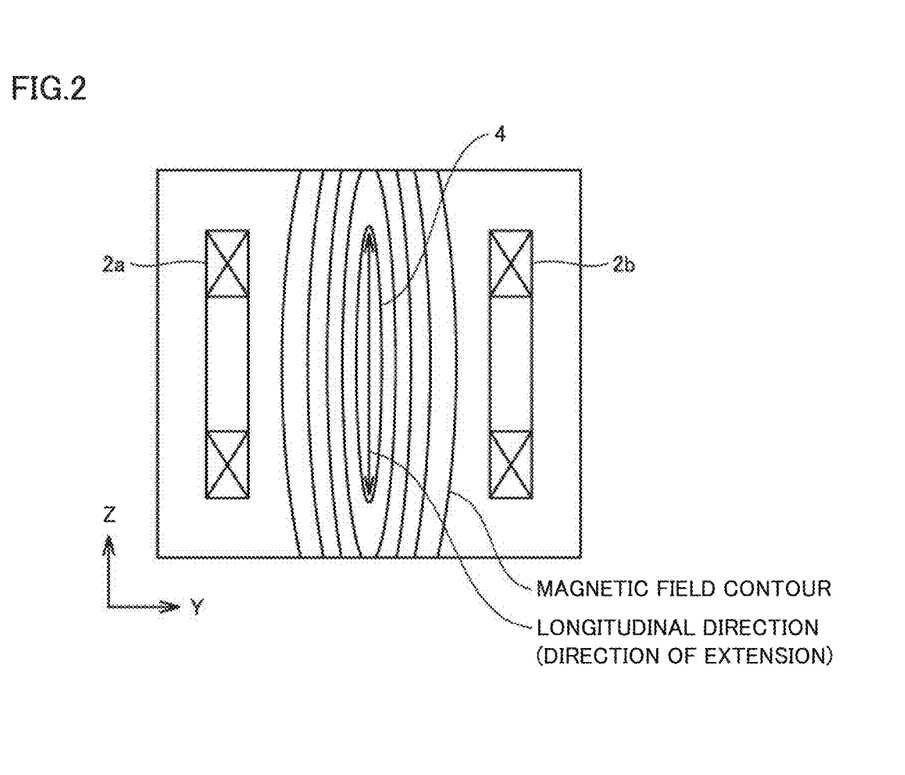
FIG. 2 shows a direction of extension of a field free line in the magnetic particle imaging system according to the embodiment.

Referring to FIGS. 1 and 2, a quadrupole magnetic field is generated as current flows through first field free region generation unit 2*a* and second field free region generation unit 2*b* of field free region generator 2 in the opposite directions. The shape of the field free region is changed by field free region generator 2. Examples of the field free point include a field free point (FFP) and a field free line (FFL). The field free point (FFP) has a magnetic field distribution which has a magnetic field gradient in three orthogonal directions and is close to a perfect circle, whereas the field free line (FFL) has a shape in which a magnetic field distribution extends elliptically, and near the examination region, has no magnetic field gradient in the longitudinal direction of the ellipse or has a magnetic field gradient much smaller than in the other two directions. It is thus regarded that the field free region extends linearly in the direction with a much smaller magnetic field gradient. Such a direction is referred to as a direction of extension of a field free line (FFL) hereinafter. Field free region generator 2 is configured to generate a field free line 4 with the direction of linear extension of the field free region as the direction of extension.

In the present embodiment in which the field free region has a linear shape, in imaging of a particle distribution, a measurement position is scanned by translating and rotating field free line 4 with respect to a subject, and an inverse problem is solved from the relation between position and signal strength, thereby reconstructing a particle distribution image. Examples of the method of scanning field free line 4 include a method of mechanically moving field free region generator 2 or a subject, a method of moving field free line 4 by adjustment of a current ratio of a field free region generator 2 composed of multiple coils, and a method of moving field free line 4 by independently rotating field free region generators 2, each of which is composed of multiple permanent magnets.

Since a measurement signal u(t) is the integral of a system function s(r,t) indicating a signal distribution function and a particle distribution c(r) as expressed by Equation 1 below, system function s(r,t) needs to be subjected to deconvolution in order to reconstruct particle distribution c(r) from measurement signal u(t). The preliminarily obtained system function s(r,t) and Equation 1 are stored in an imaging unit IP (see FIG. 5) or in a storage unit (not shown) as separate configurations. Particle distribution c(r) is obtained by deconvolution of system function s(r,t) stored in imaging unit IP or the storage unit from measurement signal u(t) measured by the magnetic sensor.

$$u(t) = \int_{object} s(r,t)c(r)dr, \text{ with } s(r,t) = -\mu_0 p(r) \cdot \frac{\partial \overline{m}(r,t)}{\partial t} \quad (1)$$

In Equation 1, p(r) represents magnetic sensor sensitivity. When the magnetic sensor is a coil, p(r)=H(r)/I based on the reciprocity theorem, and when the magnetic sensor is particularly a solenoidal coil, H=NI. Thus, magnetic sensor sensitivity is proportional to a winding density. In Equation 1, m(r,t) represents an average magnetic moment of magnetic particles. Given that a magnetization curve is expressed by Langevin function L, $m(r,t)=m^s L(\beta|H|)=m^s L(\beta\sqrt{(H_{excite}^2+H_{gradient}^2)})$, where $m^s$ represents saturation magnetization, $\beta=\mu_0 m^s/k_B T$, $\mu_0$ represents space permeability, $k_B$ represents Boltzmann constant, and T represents particle temperature. The magnetic moment depends on the external magnetic field and the magnetization curve of magnetic particles. The system function is thus a function obtained by integrating information on the excited magnetic field, the gradient magnetic field, the magnetization curve of magnetic particles, and the magnetic sensor sensitivity, and is a signal distribution indicating signals generated from respective examination sections of the examination region in which magnetic particles are distributed uniformly.

Excited magnetic field generator 1 is configured to generate an excited magnetic field 5 in field free line 4 generated by field free region generator 2. Excited magnetic field generator 1 is configured to apply an alternating-current (AC) magnetic field to the examination region. Specifically, a coil connected to an AC supply is used for excited magnetic field generator 1. A yoke may be attached to the coil. First excited magnetic field generation unit 1*a* and second excited magnetic field generation unit 1*b* are spaced from each other in the direction of extension of field free line 4. Although the direction of excited magnetic field 5 is desirably parallel to the direction of extension of field free line 4, the direction of excited magnetic field 5 may not be completely parallel to the direction of extension of field free line 4 as long as the interference between excited magnetic field 5 and the gradient magnetic field is negligible.

Magnetic sensor 3 is configured to detect a signal of a magnetic particle generated by excited magnetic field 5 generated by first excited magnetic field generation unit 1*a* and second excited magnetic field generation unit 1*b*. First magnetic sensor unit 3*a* and second magnetic sensor unit 3*b* are spaced from each other to sandwich an axis of rotation 6 in the direction of extension of field free line 4 therebetween so as to detect magnetic signals from magnetic particles excited in the direction of extension of field free line 4. First magnetic sensor unit 3a and second magnetic sensor unit 3b are spaced from each other so as to sandwich an axis of rotation 1c of excited magnetic field generator 1 therebetween. Axis of rotation 6 in the direction of extension of field free line 4 coincides with axis of rotation 1c of excited magnetic field generator 1.

The reason why first excited magnetic field generation unit 1a and second excited magnetic field generation unit 1b of excited magnetic field generator 1 are spaced from each other is that a freedom of degree can be provided to a subject size by preventing excited magnetic field generator 1 from interfering with the subject regardless of the subject size in the direction of extension of axis of rotation 6 in field free line 4. For the same reason, when a coil is used for magnetic sensor 3, first magnetic sensor unit 3a and second magnetic sensor unit 3b of magnetic sensor 3 which detect a signal of a magnetic particle generated in the same direction as that of excited magnetic field 5 are spaced from each other in the direction of extension of field free line 4. Although excited magnetic field generator 1 and magnetic sensor 3 are shown as circular coils in FIG. 1, excited magnetic field generator 1 and magnetic sensor 3 may be saddle-shaped coils.

In the present embodiment, first excited magnetic field generation unit 1a and second excited magnetic field generation unit 1b are arranged in the direction of extension of field free line 4, and excited magnetic field 5 is applied in the direction of extension of field free line 4. Thus, excited magnetic field 5 expressed by Equation 2 below does not interfere with the gradient magnetic field expressed by Equation 3 below, and the external magnetic field applied to magnetic particles is expressed by Equation 4 below.

$$H_{excite} = \begin{bmatrix} 0 \\ 0 \\ A\cos\omega t \end{bmatrix} \quad (2)$$

$$H_{gradient} = \begin{bmatrix} -Gx \\ Gy \\ 0 \end{bmatrix} \quad (3)$$

$$H = \begin{bmatrix} -Gx \\ Gy \\ A\cos\omega t \end{bmatrix}, |H| = \sqrt{G^2(x^2+y^2) + A^2\cos^2(\omega t)} \quad (4)$$

Figure 3:
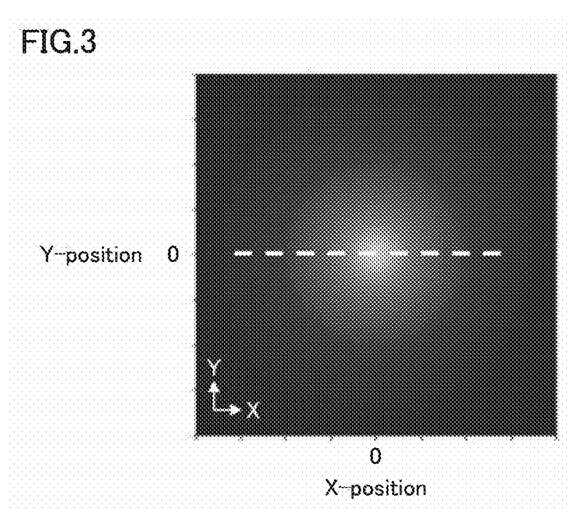
FIG. 3 is an XY sectional view of a system function of the magnetic particle imaging system according to the embodiment.
Figure 4:
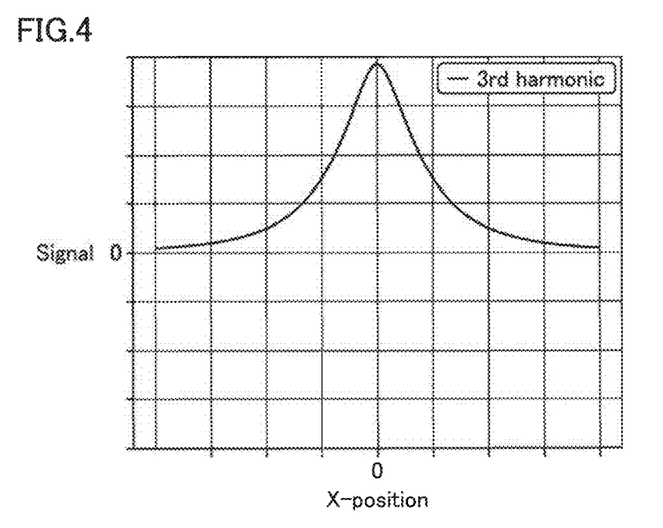
FIG. 4 is an X-direction one-dimensional profile diagram of the system function of the magnetic particle imaging system according to the embodiment.

In Equations (2) to (4), G represents the magnitude of a magnetic field gradient, A represents the magnitude of an excited magnetic field, and ω represents an angular frequency of an excited magnetic field. A minus sign in $H_{gradient}$ may be assigned to an x component or a y component. Also, a z component needs not to be completely zero, and it suffices that the field free region can be regarded as being sufficiently linear in the examination region. The x component and the y component of $H_{excite}$ also need not to be completely zero, and it suffices that the interference between the excited magnetic field and the gradient magnetic field is negligible. Thus, the system function of a third harmonic according to the embodiment is as shown in FIG. 3 (a signal distribution when magnetic particles are distributed uniformly in the examination region) and FIG. 4 (an X-direction one-dimensional profile diagram with Y=0 on the line indicated by the dotted line of FIG. 3). Herein, when superparamagnetic particles are used for magnetic particles included in the subject, the fundamental signal includes not only a particle signal but also an excited magnetic field signal, and accordingly, a third or higher-order harmonic which includes no excited magnetic field signal is treated as a particle signal. As shown in FIG. 4, since the system function has a positive value (the sign thereof does not change) in the entire region, a particle distribution can be reconstructed when there is at least one kind of high-order harmonic (e.g., only a third harmonic). The values of Equations 2 and 3 stored in the storage unit are read by a controller CP (see FIG. 5). Excited magnetic field generator 1 controls conduction of a current satisfying Equation 2. When field free region generator 2 is an electromagnet, not a permanent magnet, field free region generator 2 controls conduction of a current satisfying Equation 3 read by controller CP from the storage unit.

Figure 5:
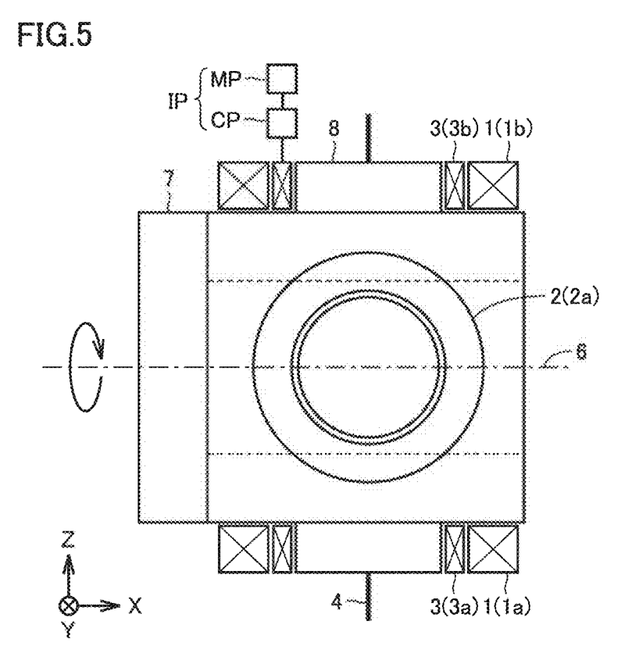
FIG. 5 is a partial sectional front view schematically showing a configuration of the magnetic particle imaging system according to the embodiment which includes an imaging unit and a rotation mechanism.

A configuration of magnetic particle imaging system 10 according to the embodiment which includes imaging unit IP and a rotation mechanism 7 will be described with reference to FIGS. 5 and 6. For the convenience of description, FIG. 5 shows cross sections of excited magnetic field generator 1 and magnetic sensor 3. For the convenience of description, FIG. 6 shows cross sections of excited magnetic field generator 1, field free region generator 2, and magnetic sensor 3.

Figure 6:
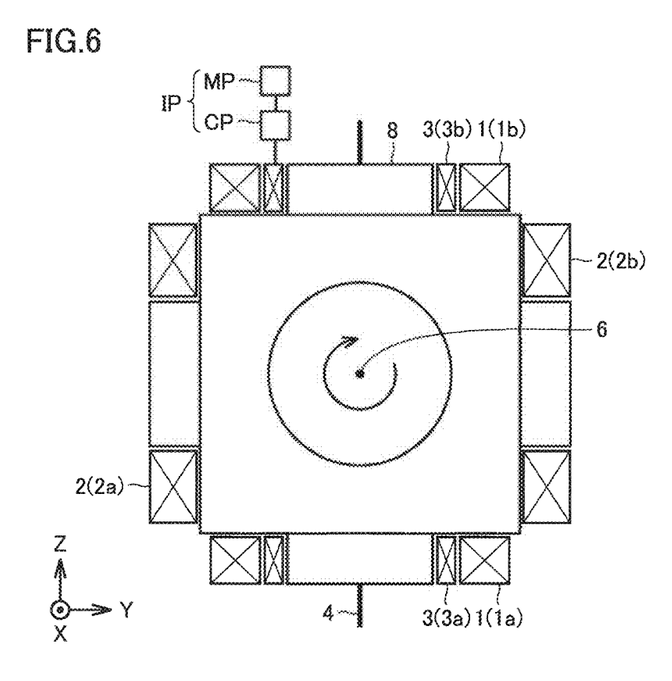
FIG. 6 is a partial lateral sectional view schematically showing the configuration of the magnetic particle imaging system according to the embodiment which includes the imaging unit and the rotation mechanism.

As shown in FIGS. 5 and 6, magnetic particle imaging system 10 according to the embodiment further includes imaging unit IP, rotation mechanism 7, and a fixing jig 8.

Imaging unit IP is configured to image magnetic particles based on a signal detected by magnetic sensor 3. Imaging unit IP includes controller CP and a monitor MP. Controller CP is configured to reconstruct a particle distribution based on the signal detected by magnetic sensor 3. Monitor MP is configured to display an image indicating a particle distribution reconstructed by controller CP.

Rotation mechanism 7 is configured to rotate excited magnetic field generator 1 with axis of rotation 6 in the direction of extension in field free line 4 as the center. Rotation mechanism 7 is connected to fixing jig 8. Fixing jig 8 is configured to fix excited magnetic field generator 1, field free region generator 2, and magnetic sensor 3. Rotation mechanism 7 is configured to rotate excited magnetic field generator 1 via fixing jig 8 with axis of rotation 6 in the direction of extension in field free line 4 as the center.

In the present embodiment, excited magnetic field 5 does not interfere with the gradient magnetic field, and accordingly, field free line 4 does not oscillate due to excited magnetic field 5. When the particle distribution in the direction of extension (X direction in FIG. 1) of axis of rotation 6 in field free line 4 is reconstructed, thus, a coil that electrically moves field free line 4 in the X direction may be provided. A mechanical drive unit (not shown) may be provided that integrally translates excited magnetic field generator 1, field free region generator 2, and magnetic sensor 3 in the direction of extension of axis of rotation 6 in field free line 4, or a mechanical drive unit (not shown) may be provided that translates the subject in the direction of extension of axis of rotation 6 in field free line 4.

A magnetic particle imaging method according to the embodiment will now be described. The magnetic particle imaging method according to the embodiment is a magnetic particle imaging method of imaging magnetic particles in a field free region using an excited magnetic field for the magnetic particles.

The magnetic particle imaging method includes a field free region generation step and an excited magnetic field generation step. The field free region generation step generates a field free line (FFL) with the direction of linear extension of the field free region as a direction of extension. The excited magnetic field generation step generates an excited magnetic field in the field free line (FFL) generated in the field free region generation step. The excited magnetic field generation step is performed by first excited magnetic field generation unit 1a and second excited magnetic field generation unit 1b spaced from each other in the direction of extension of field free line (FFL).

The functions and effects of the present embodiment will now be described by comparison with those of a comparative example.

Figure 7:
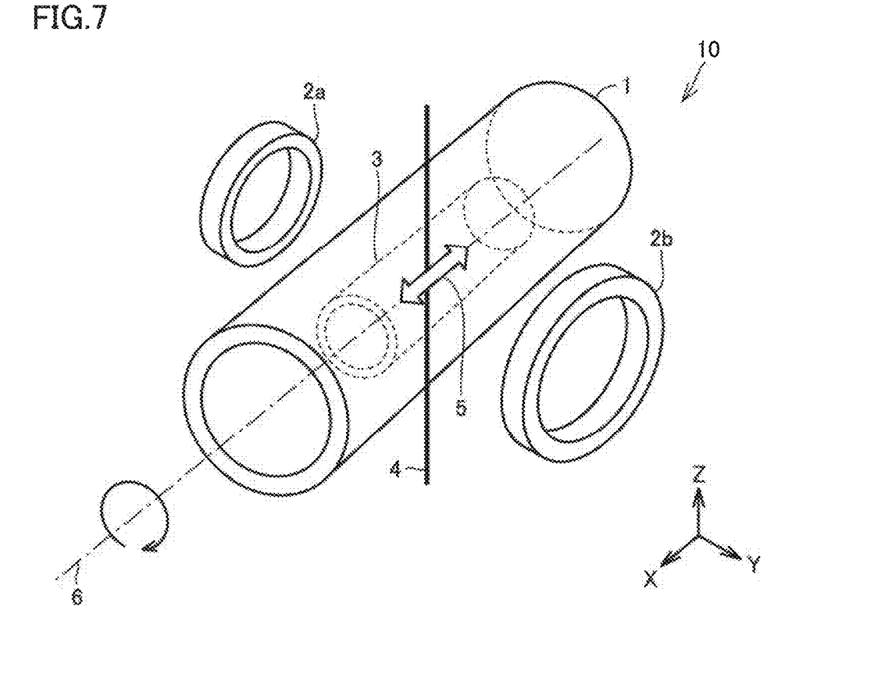
FIG. 7 is a perspective view schematically showing a configuration of a magnetic particle imaging system of a comparative example.

Magnetic particle imaging system 10 of the comparative example shown in FIG. 7 includes excited magnetic field generator 1, field free region generator 2 including first field free region generation unit 2a and second field free region generation unit 2b, and magnetic sensor 3. In this case, excited magnetic field generator 1 and magnetic sensor 3 need not to rotate. Thus, in order to maximize excitation efficiency and detection efficiency, excited magnetic field generator 1 or magnetic sensor 3 is commonly formed of an integral solenoidal coil without being divided into components.

In magnetic particle imaging system 10 of the comparative example, excited magnetic field 5 is applied in the direction (the direction perpendicular to the direction of extension of field free line 4) of the same plane (XY plane) as the gradient magnetic field. Thus, excited magnetic field 5 expressed by Equation 5 below is superimposed on the gradient magnetic field expressed by Equation 6 below while interfering with each other, and the external magnetic field applied to magnetic particles is expressed by Equation 7 below.

$$H_{excite} = \begin{bmatrix} A\cos\omega t \\ 0 \\ 0 \end{bmatrix} \quad (5)$$

$$H_{gradient} = \begin{bmatrix} -Gx \\ Gy \\ 0 \end{bmatrix} \quad (6)$$

$$H = \begin{bmatrix} -Gx + A\cos\omega t \\ Gy \\ 0 \end{bmatrix}, |H| = \sqrt{G^2(x^2 + y^2) + A^2\cos^2(\omega t) - 2GAx\cos(\omega t)} \quad (7)$$

Note that the minus sign in $H_{gradient}$ may be assigned to the x component or the y component, and $A\cos\omega t$ in $H_{excite}$ may be the x component or the y component.

Figure 8:
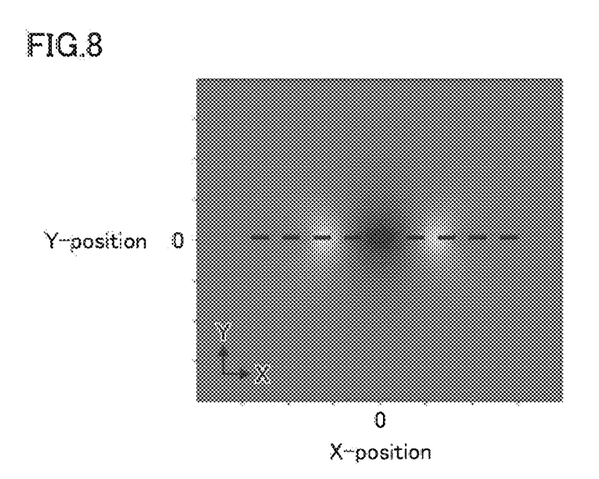
FIG. 8 is an XY sectional view of a system function of the magnetic particle imaging system of the comparative example.
Figure 9:
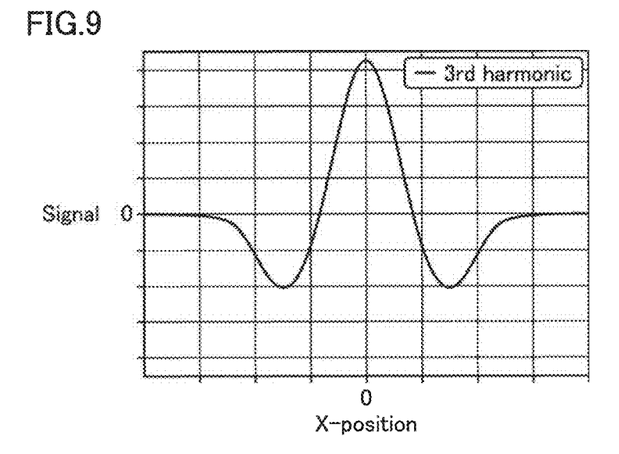
FIG. 9 is an X-direction one-dimensional profile diagram of the system function of the magnetic particle imaging system of the comparative example.

In magnetic particle imaging system 10 of the comparative example shown in FIG. 7, field free line 4 oscillates in the X direction due to the interference between excited magnetic field 5 and the gradient magnetic field, and accordingly, the system function in the X direction serves as a function that oscillates across the positive and negative values, as shown in FIGS. 8 and 9. In this case, a correct image cannot be obtained merely by reconstructing a particle distribution image with one kind of high-order harmonic (e.g., only third harmonic), and blurring or artifact occurs (particularly in the X direction). Thus, harmonic signals of up to several orders are required to correctly reconstruct an image with the configuration of the comparative example, but such reconstruction is practically difficult because a higher order has a lower signal strength.

Further, in magnetic particle imaging system 10 of the comparative example, measurement signals counteract each other in the positive region and the negative region of the system function, thus leading to a lower signal strength. For example, when there is a sample having a uniform distribution completely across the oscillation region of the system function, signals counteract each other completely, and accordingly, the signals cannot be obtained. It is thus impossible to reconstruct a ZY cross section.

In magnetic particle imaging system 10 according to the present embodiment, first excited magnetic field generation unit 1a and second excited magnetic field generation unit 1b are spaced from each other in the direction of extension of field free line 4. Excited magnetic field 5 is thus provided in the direction of extension of field free line 4, and accordingly, excited magnetic field 5 does not interfere with the gradient magnetic field. As a result, the system function has a positive value (the sign thereof does not change) in the entire region, thus enabling reconstruction of a particle distribution from a high-order harmonic component of at least one order.

Thus, blurring or artifact of a reconstructed image can be solved merely by obtaining a signal of at least one kind of high-order harmonic. Also, since the system function has a simple shape as shown in FIG. 4, an image can be reconstructed by maximum likelihood-expectation maximization (ML-EM) or any other common inverse problem solving method used in X-ray computed tomographic image (CT) or magnetic resonance imaging (MRI).

Since the system function has a positive value (the sign thereof does not change) in the entire region, measurement signals do not counteract each other in the positive region and the negative region of the system function. This leads to a higher signal strength.

In magnetic particle imaging system 10 according to the present embodiment, magnetic particles can be imaged by imaging unit IP based on a signal detected by magnetic sensor 3.

In magnetic particle imaging system 10 according to the present embodiment, excited magnetic field generator 1 can be rotated by rotation mechanism 7 with axis of rotation 6 in the direction of extension in field free line 4 as the center. This enables rotation of excited magnetic field 5 in conformity with the rotation of field free line 4. One example of the method of rotating excited magnetic field 5 is a method of electrically rotating excited magnetic field 5 with multiple coils, and such a method requires complicated control reflecting changes in the characteristics per coil in order to maintain accuracy. Compared with the above method, the method of mechanically rotating excited magnetic field generator 1 can thus maintain a relative positional relationship in an easy and simple manner and reduce interference with the gradient magnetic field of excited magnetic field 5.

In magnetic particle imaging system 10 according to the present embodiment, first magnetic sensor unit 3a and second magnetic sensor unit 3b are spaced from each other so as to sandwich axis of rotation 6 in the direction of extension of field free line 4 therebetween. This enables detection of a magnetic signal from magnetic particles excited in the direction of extension of field free line 4 by first magnetic sensor unit 3a and second magnetic sensor unit 3b.

The magnetic particle imaging method according to the present embodiment can reconstruct a particle distribution from a high-order harmonic component of at least one order.

Although the present disclosure has been described and illustrated in detail, it is clearly understood that the same is by way of illustration and example only and is not to be taken by way of limitation, the scope of the present disclosure being interpreted by the terms of the appended claims.

What is claimed is:

1. A magnetic particle imaging system that images magnetic particles in a field free region using an excited magnetic field for the magnetic particles, the magnetic particle imaging system comprising:
   a field free region generator to generate a field free line with a direction of linear extension of the field free region as a direction of extension; and
   an excited magnetic field generator to generate the excited magnetic field in the field free line generated by the field free region generator, wherein
   the excited magnetic field generator includes a first excited magnetic field generation unit and a second excited magnetic field generation unit, and
   the first excited magnetic field generation unit and the second excited magnetic field generation unit are spaced from each other in the direction of extension of the field free line.

2. The magnetic particle imaging system according to claim 1, further comprising:
   a magnetic sensor to detect a signal of the magnetic particles generated by the excited magnetic field generated by the first excited magnetic field generation unit and the second excited magnetic field generation unit; and
   an imaging unit to image the magnetic particles based on the signal detected ty the magnetic sensor.

3. The magnetic particle imaging system according to claim 2, further comprising a rotation mechanism to rotate the excited magnetic field generator with an axis of rotation in the direction of extension of the field free line as a center.

4. The magnetic particle imaging system according to claim 3, wherein
   the magnetic sensor includes a first magnetic sensor unit and a second magnetic sensor unit, and
   the first magnetic sensor unit and the second magnetic sensor unit are spaced from each other so as to sandwich the axis of rotation in the direction of extension of the field free line therebetween.

5. A magnetic particle imaging method of imaging magnetic particles in a field free region using an excited magnetic field for the magnetic particles, the method comprising:
   a field free region generation step of generating a field free line with a direction of linear extension of the field free region as a direction of extension; and
   an excited magnetic field generation step of generating the excited magnetic field in the field free line generated in the field free region generation step,
   wherein the excited magnetic field generation step is performed by a first excited magnetic field generation unit and a second excited magnetic field generation unit spaced from each other in the direction of extension of the field free line.

6. The magnetic particle imaging system according to claim 1, wherein the excited magnetic field generator is configured to apply an alternating-current (AC) magnetic field to an examination region.

7. The magnetic particle imaging system according to claim 1, wherein:
   the field free generator is configured to generate a gradient magnetic field; and
   the excited magnetic field generator is configured to generate the excited magnetic field along a direction that minimizes interference with the gradient magnetic field.

8. The magnetic particle imaging system according to claim 1, wherein:
   the field free generator is configured to generate a gradient magnetic field; and
   the excited magnetic field generator is configured to generate the excited magnetic field along a direction that is parallel to the direction of extension of the field free line.

9. The magnetic particle imaging system according to claim 1, wherein:
   the field free generator is configured to generate a gradient magnetic field; and
   the excited magnetic field generator is configured to generate the excited magnetic field along a direction that does not interfere with the gradient magnetic field.

10. The magnetic particle imaging system according to claim 3, the rotation mechanism rotates the excited magnetic field generator while maintaining a positional relationship between the excited magnetic field generator and the field free line.

* * * * *